United States Patent [19]  [11] 4,316,815
Mercer et al.  [45] Feb. 23, 1982

[54] BIS-TRIAZOLYL AND BIS-PYRAZOLYL STILBENE COMPOUNDS

[75] Inventors: Alec V. Mercer, Bramhope; Roger Paver, Eldwick, both of England

[73] Assignee: Sandoz Ltd., Basel, Switzerland

[21] Appl. No.: 206,328

[22] Filed: Nov. 12, 1980

[30] Foreign Application Priority Data

Nov. 14, 1979 [GB] United Kingdom ............... 39349/79
Jun. 23, 1980 [GB] United Kingdom ............... 20472/80

[51] Int. Cl.$^3$ .................. C07D 403/14; C07D 405/14; C07D 413/14
[52] U.S. Cl. .............................. 252/301.22; 542/435; 542/436
[58] Field of Search ............................. 542/435, 436; 252/301.22

[56] References Cited

U.S. PATENT DOCUMENTS 3,796,706  3/1974  Hausermann et al. ............... 542/462
3,928,329  12/1975  Fleck et al. ..................... 252/301.22
4,167,626  9/1979  Fleck et al. ........................ 542/435

FOREIGN PATENT DOCUMENTS 1149286  4/1969  United Kingdom .
1459307  12/1976  United Kingdom .
1520633  8/1978  United Kingdom .

Primary Examiner—Arthur P. Demers
Attorney, Agent, or Firm—Gerald D. Sharkin; Richard E. Vila; Thomas C. Doyle

[57] ABSTRACT

The invention relates to stilbene derivatives which are used as optical brightening agents, particularly as anionic brightening agents for polyamide and cellulosic substrates. These stilbene derivatives have the formula I

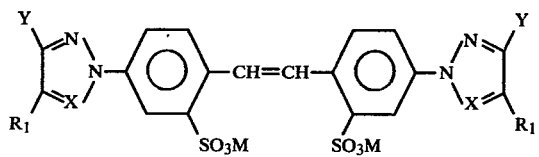

in which
both X's are the same and are $CR_5$ or N, where $R_5$ is hydrogen, $C_{1-4}$alkyl or phenyl;
both Y's are the same and are each one of the radicals of benzofuran, triazole, pyrazole, dibenzofuran or dibenzothiophene and benzothiophene, and
$R_1$ is as defined in the specification.

10 Claims, No Drawings

BIS-TRIAZOLYL AND BIS-PYRAZOLYL STILBENE COMPOUNDS

The invention relates to stilbene derivatives.
The invention provides compounds of formula I,

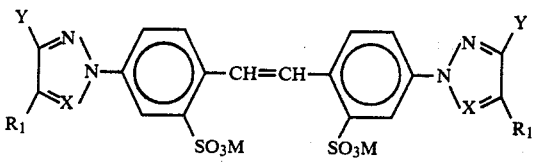

I in which
both $R_1$'s are the same and are hydrogen, $C_{1-4}$alkyl, bromine, chlorine, —COOM, —CONR$_2$R$_3$, —COOR$_4$, —CN, —SO$_3$M, —SO$_2$NR$_2$R$_3$ or —SO$_2$R$_4$, where $R_2$ and $R_3$ independently are hydrogen, $C_{1-4}$alkyl or phenyl with the proviso that only one may be phenyl or $R_2$ and $R_3$, together with the nitrogen to which they are attached, form a five or six membered heterocyclic ring and $R_4$ is $C_{1-4}$alkyl or phenyl;
both X's are the same and are CR$_5$ or N, where $R_5$ is hydrogen, $C_{1-4}$alkyl or phenyl;
both Y's are the same and are each one of the radicals of formulae (a) to (e)

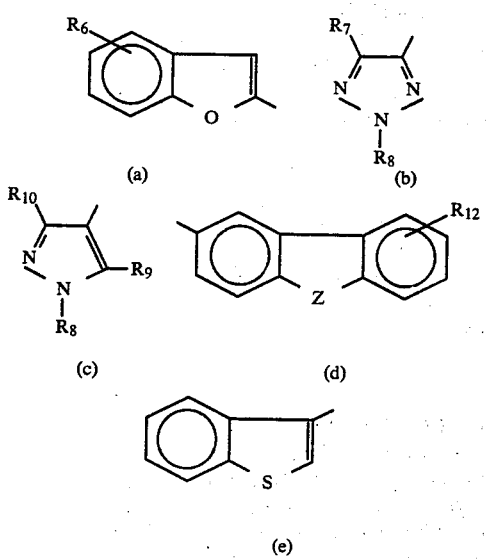

with the proviso that the Y's are not radical (b) when X=N, $R_6$ is hydrogen, chlorine, $C_{1-4}$alkoxy, $C_{1-4}$alkyl, —SO$_3$M or phenyl, $R_7$ is hydrogen or $C_{1-4}$alkyl, $R_8$ is an aryl radical unsubstituted or substitued by up to two substituents selected from $C_{1-4}$alkyl, $C_{1-4}$alkoxy, chlorine, cyano, —COOM, —COOR$_4$, —CONR$_2$R$_3$, —SO$_2$NR$_2$R$_3$, —SO$_2$R$_4$ and —SO$_3$M with the proviso that where the aryl radical is substituted by two substituents at least one of the substituents is $C_{1-4}$alkyl, $C_{1-4}$alkoxy or chlorine, $R_9$ and $R_{10}$ independently are hydrogen or $C_{1-4}$alkyl; $R_{12}$ is H or —SO$_3$M and Z is O or S; and
M is hydrogen or a non-chromophoric cation.

In the compounds of formula I, $R_1$ is preferably $R_1'$ where $R_1'$ is hydrogen, methyl, chlorine, —COOM, —SO$_3$M or —COOR$_4$
When X is N, $R_1$ is more preferably $R_1''$ where $R_1''$ is hydrogen, —COOM, or —COOR$_4'$ where $R_4'$ is $C_{1-4}$alkyl, and when X is CR$_5$, $R_1$ is $R_1'''$ where $R_1'''$ is hydrogen or —SO$_3$M.

When $R_2$ and $R_3$ together with the nitrogen atom to which they are attached form a ring, this is preferably a five or six membered saturated ring, and is more preferably a piperidine or morpholine ring.

Preferably, $R_4$ is $R_4'$ where $R_4'$ is defined above, more preferably $R_4$ is $R_4''$ where $R_4''$ is methyl or ethyl.

Preferably X is X' where X' is CR$_5'$ or N where $R_5'$ is hydrogen or methyl; more preferably X is CH.

Preferably $R_5$ is $R_5'$ where $R_5'$ is defined above, more preferably $R_5$ is hydrogen.

Preferably $R_6$ is $R_6'$ where $R_6'$ is hydrogen, chlorine, $C_{1-4}$alkyl, or $C_{1-4}$alkoxy; more preferably $R_6$ is $R_6''$ where $R_6''$ is hydrogen, chlorine, methyl or methoxy; most preferably $R_6$ is hydrogen.

Preferably $R_7$ is $R_7'$ where $R_7'$ is hydrogen or methyl, more preferably methyl.

Preferably $R_8$ is $R_8'$ where $R_8'$ is phenyl or naphthyl unsubstituted or substituted by 1 or 2 substituents selected from $C_{1-4}$alkyl, $C_{1-4}$alkoxy, chlorine or —SO$_3$M with the proviso that when disubstituted both substituents cannot be —SO$_3$M; more preferably $R_8''$ is phenyl, unsubstituted or monosubstituted by methyl, methoxy, chlorine or —SO$_3$M; most preferably $R_8$ is unsubstituted phenyl.

$R_9$ and $R_{10}$ are preferably $R_9'$ and $R_{10}'$ where $R_9'$ and $R_{10}'$ independently are hydrogen or methyl.

Preferably Y is Y' where each Y' is one of the radicals a' to d' below

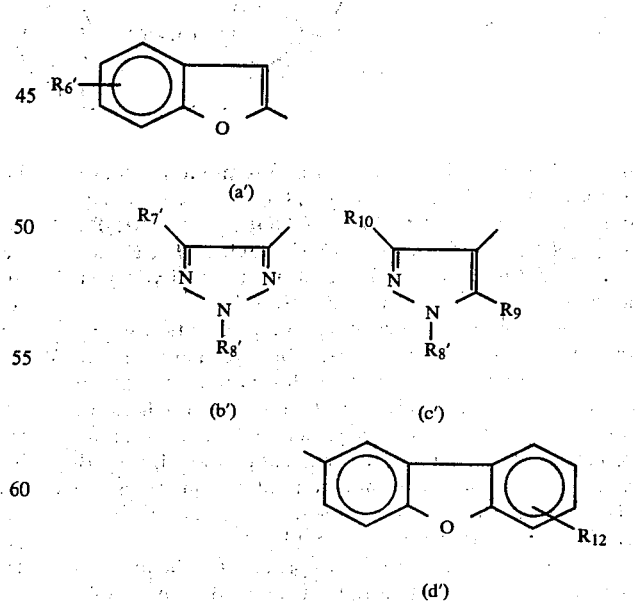

where $R_6'$, $R_7'$, $R_8'$, $R_9$ $R_{10}$ and $R_{12}$ are defined above.

More preferably Y is Y'' where each Y'' is one of the radicals a'' to c'' below or d' above

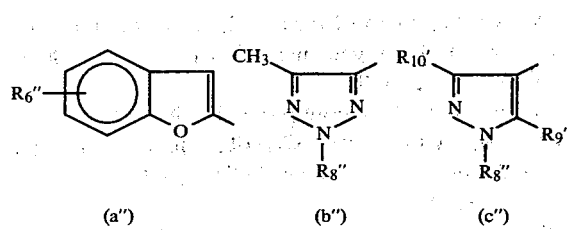

(a″) (b″) (c″)

where $R_6''$, $R_8''$, $R_9'$ and $R_{10}'$ are defined above.

All alkoxy groups are preferably methoxy, $R_4$ as alkyl is preferably methyl or ethyl and all other alkyl groups are preferably methyl.

A preferred class of compounds according to the invention is of the formula I′

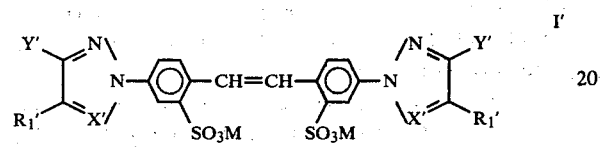

in which $R_1'$, $X'$ and $Y'$ are above defined.

A more preferred class of compounds according to the invention is of the formula I″

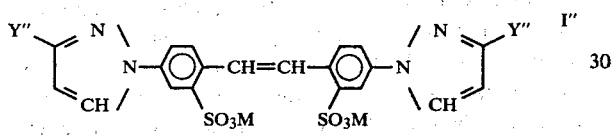

where Y″ is above defined.

Further according to the invention there is provided a compound of formula X

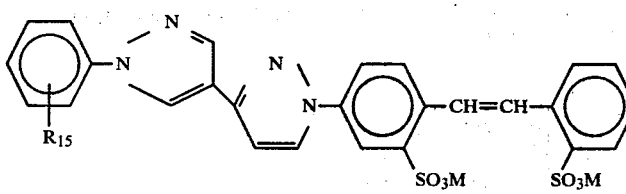

in which M is hydrogen or a non-chromophoric cation and the groups $R_{15}$ are hydrogen, $C_{1-4}$alkyl, $C_{1-4}$alkoxy, chlorine, cyano, —COOM, —COOR$_4$, —CONR$_2$R$_3$, —SO$_2$NR$_2$R$_3$, —SO$_2$R$_4$, —SO$_3$M in which $R_2$, $R_3$ and $R_4$ are defined above. Preferably $R_{15}$ is hydrogen, methyl, methoxy, chlorine, or —SO$_3$M.

In the compounds according to the invention where the M's signify cations the exact nature thereof is not critical provided they are non-chromophoric. Cations conventional in the optical brightening art, to which the present invention relates, may be employed. Examples of suitable cations are alkali-metal cations, alkaline earth metal cations and the ammonium, alkylammonium and alkanolammonium cations. Alkali metal cations, especially the sodium cation, are preferred.

The invention also provides a process for the production of compounds of formula I, defined above, comprising (a) obtaining a compound of formula I where X is CR$_5$, preferably CH, by
oxidising a compound of formula II,

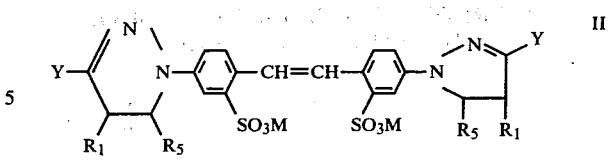

(b) obtaining a compound of formula I, in which X is N, by
(bi) cyclising a compound of formula IV

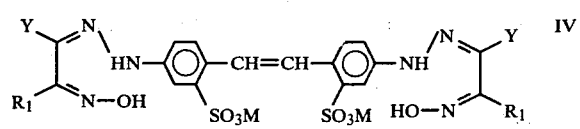

(bii) reducing a compound of formula V

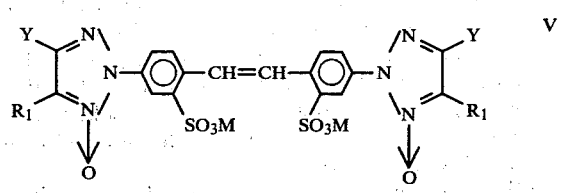

or (biii) cyclising a compound of formula VI

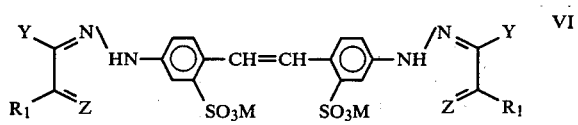

where Z is NH or O, and in which $R_1$, Y and M are above defined.

The process may be carried out in conventional manner. Process (a) is suitably carried out in an inert solvent, e.g. in water, in an inert organic solvent or in a mixture of such solvent with water. Suitable organic solvents include dimethylformamide, acetic acid, 2-ethoxy- or -methoxy-ethanol, iso-propanol or pyridine. Suitable oxidising agents include manganese dioxide, air (optionally in the presence of heavy metal oxidation catalysts, such as cupric salts) sodium hypochlorite, sodium hypobromite, lead dioxide, lead tetra-acetate, Raney nickel, alkali or ammonium polysulphides, potassium ferricyanide, hydrogen peroxide, persulphates, percarbonates or perborates. A suitable reaction temperature is from 0° to 200° C., preferably from 20° C. to 150° C.

Process (bi) is suitably carried out employing a dehydrating agent. Suitable dehydrating agents include the anhydrides of organic acids, e.g. acetic and propionic anhydride, preferably in the presence of a salt of an organic acid, e.g. sodium or potassium acetate. Other suitable dehydrating agents include the phosphorus halides, e.g. phosphorus trichloride, the phosphorus oxyhalides, e.g. phosphorus oxychloride, organic isocyanates and phosgene. The reaction is suitably carried out in an inert solvent, e.g. in dimethylformamide or pyridine, or, where liquid under the reaction conditions, in an excess of the dehydrating agent. The cyclisation using the dehydrating agent is conveniently carried out at a temperature of from 0° to 200° C., preferably 30° to 130° C.

Alternatively, the cyclisation may be carried out by heating the compounds of formula IV, in the presence of urea, to a temperature of from 90° C. to 210° C., preferably from 130° C. to 180° C. This reaction may be carried out in an inert solvent, e.g. in ethylene glycol, diethylene glycol or sulpholane, but is more preferably carried out employing an excess of the urea, the reaction taking place in the melt.

The reduction process (bii) is conveniently carried out using such reducing agents as zinc dust/acetic acid, zinc dust/sodium hydroxide and iron/acetate acid. Suitable solvents include water, organic solvents and mixtures of water and organic solvent, suitable organic solvents being methanol, ethanol, isopropanol, 2-ethoxy- or 2-methoxy-ethanol, dimethylformamide and pyridine. Hydrogen chloride may also be employed to reduce the compounds of formula V, although this tends to lead to chlorinated products. Suitable solvents for this reduction are aqueous/organic solvents such as of dioxan or diethyleneglycol dimethylether, a suitable reaction temperature being from 80° to 120° C.

In process (biii) the cyclisation is suitably carried out using a cupric salt, such as cupric chloride, cupric bromide, cupric sulphate or cupric acetate, in the presence of excess ammonia, e.g. as concentrated aqueous ammonia or a stream of ammonia, when Z signifies NH, or in the presence of an ammonium salt of an organic acid, e.g. ammonium acetate, formate or propionate, when Z signifies O. In the reaction, an excess of the cupric salt would normally be used but, if desired, the reaction can be carried out in the presence of catalytic amounts thereof if a stream of air or oxygen is passed through the reaction medium. The reaction is carried out in an inert solvent, suitably in water, an organic solvent or a mixture of water and an organic solvent, such as in aqueous methanol, pyridine, ethanol, 2-ethoxyethanol or dimethyl formamide. A suitable reaction temperature is from 20° to 200° C., preferably from 70° to 130° C.

As will be appreciated, interconversions from one compound of formula I to another may be carried out. For example, acid groups may be converted into ester or amide groups in conventional manner, and —SO₃M groups introduced into aryl radicals e.g. by treatment with hot concentrated sulphuric acid. Similarly, compounds of formula I in which M is hydrogen may be converted into compounds in which M is a cation, or vice versa, in the same conventional manner as that for the interconversion between cations M.

The resulting compounds of formula I may be isolated and purified in conventional manner.

The compounds of formula II, employed as starting materials in process (a) may be obtained, for example, by reaction of 4,4'-bis-hydrazino-stilbene-2,2'-disulphonic acid, or salts thereof, with a compound of formula VIII,

$$Y-\overset{O}{\underset{\|}{C}}-T \qquad \text{VIII}$$

where Y is as defined above, and either T is —CR₁=CR₅H or —CHR₁—CHR₅Z°, where Z° is chlorine, bromine or a substituted or unsubstituted amino group.

This process is suitably carried out in an inert solvent e.g. water, an inert organic solvent or a mixture of such a solvent with water. Suitable organic solvents include dimethylformamide, 2-ethoxy- or -methoxy ethanol, iso-propanol ethanol or pyridine. A suitable reaction temperature is 0° to 200° C. preferably 20° to 150° C. Where however, the T signifies —CHR₁—CHR₅Z°, the process is advantageously carried out in the presence of a proton acceptor such as sodium carbonate or acetate.

The compounds of formula V, employed in process (bii), are suitably obtained by oxidative cyclisation of compounds of formula IV. Suitable oxidising agents include sodium dichromate, hydrogen peroxide and cupric salts, e.g. cupric sulphate. The oxidative cyclisation is suitably carried out in water, inert organic solvents or in a mixture of such solvents with water. Suitable organic solvents include dimethylformamide, phosphoric acid trisdimethylamide, sulphones, e.g. tetramethylene sulphone, and organic bases such as pyridine. Suitable reaction temperatures are from 20° to 130° C., preferably from 60° to 110° C.

The compounds of formulae IV, VI and VIII are either known or may be obtained in conventional manner from available starting materials.

The compounds of formula I are optical brightening agents and are indicated for use in the brightening of substrates brightenable using anionic brightening agents, particularly for polyamide, e.g. synthetic polyamides such as the nylons, and cellulosic, e.g. cotton, substrates. The compounds may, for example, be applied using conventional exhaust procedures or by continuous methods such as by the so-called "Thermosol" process (Gunn & Nightingale, "Cotton and Man-Made Fibers Year Book" 1966-67, p. 410). The amount of compound employed is generally in the range of 0.01% to 1%, preferably 0.05% to 0.5%, based on the weight of the substrate. When applied by exhaust techniques, the application is conveniently carried out at a liquor to goods ratio of from 10:1 to 100:1. The brightenings obtained have notable light-fastness.

The compounds of the invention are also suitable for application under wash bath conditions onto cotton in the presence of detergents. They are particularly valuable because of their stability to bleaching agents for example sodium hypochlorite, sodium perborate and peracetic acid. The compounds may be incorporated into solid or liquid detergent compositions in amounts from 0.01 up to 3% by weight preferably 0.05 to 1.0% by weight of the composition.

In this Specification where groups are capable of bearing substituents they are unsubstituted unless indicated to the contrary.

The following Examples, in which all parts and percentages are by weight, unless otherwise stated and all temperatures in degrees Centigrade, illustrate the invention.

EXAMPLE 1

Preparation of a pyrazole of the formula

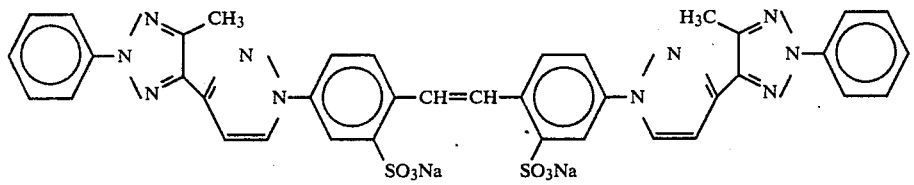

(a) The 2-phenyl-4-methyl-5-acetyl-γ-triazole was prepared by the following procedure:

Imino-acetyl acetone (99 g) was mixed with ethyl alcohol (300 ml), anhydrous sodium acetate (500 g), water (1100 ml) and anhydrous sodium carbonate (132 g). The mixture was treated at 20° with a diazonium solution prepared from aniline (93 g), concentrated hydrochloric acid S.G. 1.18 (210 ml), water (810 ml) and sodium nitrite (70 g). The mixture was stirred 1 hour at 20°, filtered and the yellow coloured imino hydrazone of formula

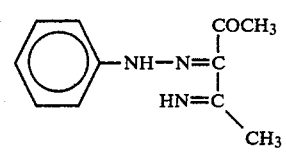

washed with water (3000 ml).

181.5 g (on a dry basis) of the imino hydrazone was mixed with ethyl alcohol (763 ml), acetic acid (305 ml), conc. ammonia (270 ml) S.G. 0.880 and cupric chloride dihydrate (251 g). The mixture was refluxed 18 hours and the ethanol removed by distillation. Toluene (883 ml) was added and the lower aqueous layer separated. The toluene layer was washed with water (500 ml) and then dried over sodium sulphate. The toluene was removed by evaporation to leave 2-phenyl-4-methyl-5-acetyl-γ-triazole as a brown crystalline solid which was recrystallised from ethyl alcohol to give pale fawn coloured needles m.p. 55°–56°.

(b) Then 2-phenyl-4-methyl-5-(β-morpholinopropionyl)-γ-triazole hydrochloride was prepared by the following procedure:

2-Phenyl-4-methyl-5-acetyl-γ-triazole (60.3 g), paraformaldehyde (10 g), morpholine hydrochloride (37 g) and 2-ethoxy ethanol (90 ml), were mixed and heated at reflux for 90 minutes. The reaction mixture was cooled to −10°, filtered and the white coloured solid washed with ethyl alcohol (100 ml). The solid was dried at 70° to give 2-phenyl-4-methyl-5-(β-morpholinopropionyl)-γ-triazole hydrochloride

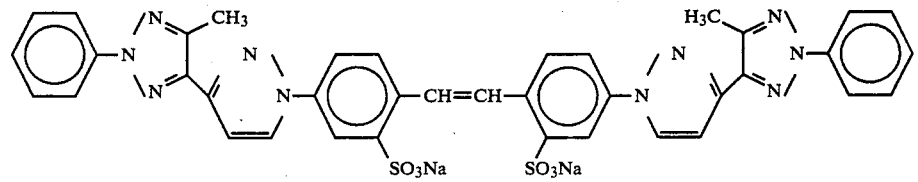

m.p. 215°–220° C.

(c) Finally 4,4′-bis-hydrazino stilbene-2,2′-disulphonic acid (44 g), water (550 ml), 2-ethoxyethanol (550 ml), sodium carbonate (36 g) and 2-phenyl-4-methyl-5-(β-morpholinopropionyl)-γ-triazole hydrochloride (77.7 g) were mixed and heated at reflux for 6 hours. The orange coloured suspension was cooled to 20°, filtered and the orange coloured pyrazoline washed with water (200 ml) and dried at 70°.

The resulting pyrazoline (90 g) was mixed with water (200 ml), dimethylformamide (300 ml) and acetic acid (150 ml) and manganese dioxide (30 g) added. The reaction mixture was refluxed for 16 hours and filtered whilst still hot. The filtrate was cooled to 5° and the yellow coloured product filtered and recrystallised from a mixture of water (200 ml) and pyridine (200 ml) to give the pyrazole of formula as a yellow coloured powder.

EXAMPLES 2–14

By using similar procedures to that described in Example 1 but starting from the appropriate starting materials the following pyrazole triazoles of general formula

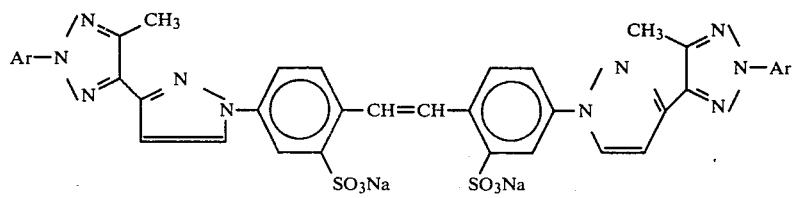

may be obtained.

| Example No. | Ar | Appearance |
|---|---|---|
| 2 | 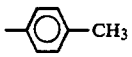 | yellow powder |
| 3 | 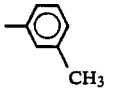 | Lemon coloured powder |
| 4 | 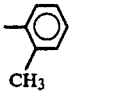 | Yellow powder |
| 5 | 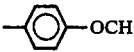 | Pale yellow powder |
| 6 | 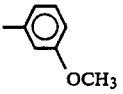 | Yellow powder |
| 7 | 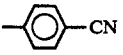 | Yellow powder |
| 8 | 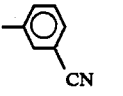 | Pale yellow powder |
| 9 | 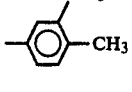 | Pale yellow powder |
| 10 | 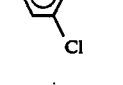 | Lemon coloured powder |
| 11 | 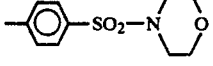 | Yellow powder |
| 12 | 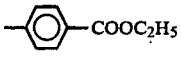 | Yellow powder |
| 13 | 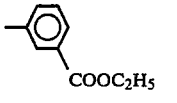 | Pale yellow powder |
| 14 | 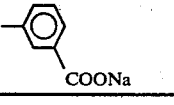 | Pale yellow powder |

EXAMPLE 15

The preparation of a compound of formula

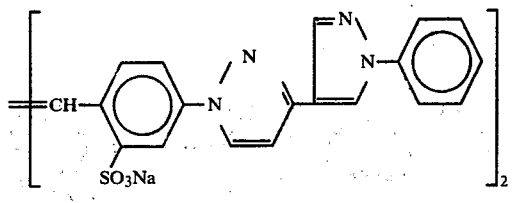

(a) 1-Phenyl-4-acetyl-pyrazole was prepared by acetylation of 1-phenyl-pyrazole with acetic anhydride according to the procedure described in Chemical Abstracts Vol. 63, 16332.

(b) 1-Phenyl-4-($\beta$-morpholinopropionyl)-pyrazole hydrochloride was prepared by the following procedure:

1-Phenyl-4-acetyl pyrazole (17.9 g) was mixed with paraformaldehyde (3.2 g), morpholine hydrochloride (11.71 g) and cellosolve (37 ml). The mixture was refluxed for 30 minutes and then cooled to 5° C. The white coloured Mannich Base was filted and washed with ethyl alcohol (100 ml) and acetone (50 ml). The white solid was dried at 70° C. to give 1-phenyl-4-($\beta$-morpholinopropionyl)-pyrazole hydrochloride

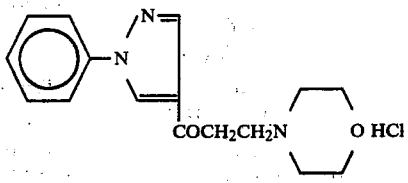

m.p. 212°–214° C.

The pyrazole of formula

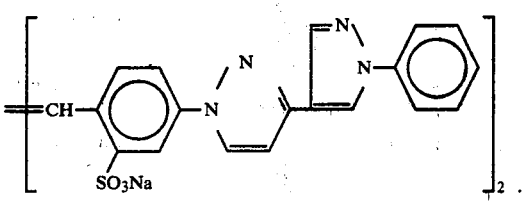

a lemon coloured powder, was prepared from 1-phenyl-4-($\beta$-morpholino-propionyl)-pyrazole hydrochloride according to the method of part (c) of Example 1 where the 1-phenyl-4-($\beta$-morpholino-propionyl) pyrazole hydrochloride is substituted for the hydrochloride of Example 1.

EXAMPLES 16 to 40

By using similar procedures to that described in Example 15 but starting from the appropriate starting materials the following pyrazole pyrazoles of general formula

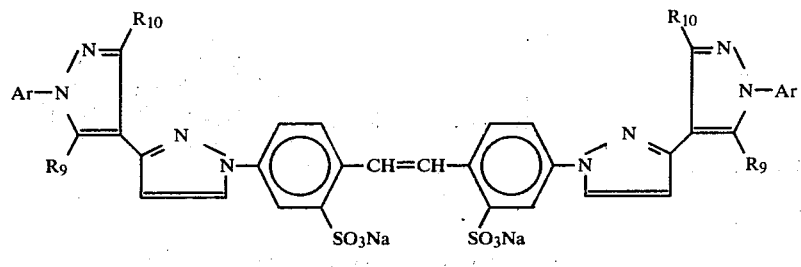

may be obtained.

| Example No. | R$_9$ | R$_{10}$ | Ar | Appearance |
|---|---|---|---|---|
| 16 | H | H | —⌬—CH$_3$ | pale yellow powder |
| 17 | H | H | —⌬ (CH$_3$ meta) | lemon coloured powder |
| 18 | H | H | —⌬—OCH$_3$ | yellow powder |
| 19 | H | H | —⌬ (OCH$_3$ meta) | lemon coloured powder |
| 20 | H | H | —⌬—Cl | yellow powder |
| 21 | H | H | —⌬ (Cl meta) | lemon coloured powder |
| 22 | H | H | —⌬—CN | yellow powder |
| 23 | H | H | —⌬ (CN meta) | pale yellow powder |
| 24 | H | H | —⌬—COOC$_2$H$_5$ | yellow powder |
| 25 | H | H | —⌬ (COOC$_2$H$_5$ meta) | pale yellow powder |
| 26 | H | H | —⌬—COONa | yellow powder |
| 27 | H | H | —⌬ (COONa meta) | yellow powder |
| 28 | CH$_3$ | CH$_3$ | —⌬ | lemon yellow powder |
| 29 | CH$_3$ | CH$_3$ | —⌬ (CH$_3$ meta) | yellow powder |
| 30 | CH$_3$ | CH$_3$ | —⌬—CH$_3$ | yellow powder |
| 31 | CH$_3$ | CH$_3$ | —⌬—Cl | yellow powder |
| 32 | H | CH$_3$ | —⌬ | lemon yellow powder |
| 33 | H | CH$_3$ | —⌬—Cl | yellow powder |
| 34 | H | CH$_3$ | —⌬ (CH$_3$ meta) | yellow powder |
| 35 | H | CH$_3$ | —⌬—CH$_3$ | yellow powder |
| 36 | CH$_3$ | H | —⌬ | lemon yellow powder |
| 37 | CH$_3$ | H | —⌬—OCH$_3$ | yellow powder |
| 38 | CH$_3$ | H | —⌬—CH$_3$ | yellow powder |
| 39 | CH$_3$ | H | —⌬ (Cl meta) | yellow powder |
| 40 | CH$_3$ | H | —⌬ (Cl meta, CH$_3$ meta) | yellow powder |

EXAMPLE 41

9.6 g of the compound prepared in Example 1 were dissolved at 75°, while stirring, in 30 ml concentrated sulphuric acid (S.G. 1.84). The sulphonation mixture was subsequently stirred for five hours at 105°–110°, then cooled to 40° and poured into 120 g ice. 20 g sodium chloride was added and after cooling to ca. 10°, the precipitate filtered off, dissolved in 150 ml hot water and the resultant solution neutralised with 30% W/W sodium hydroxide solution. 15 g sodium chloride was added and the mixture cooled to 0°. The precipitated product was filtered off and dried to give the triazole of formula

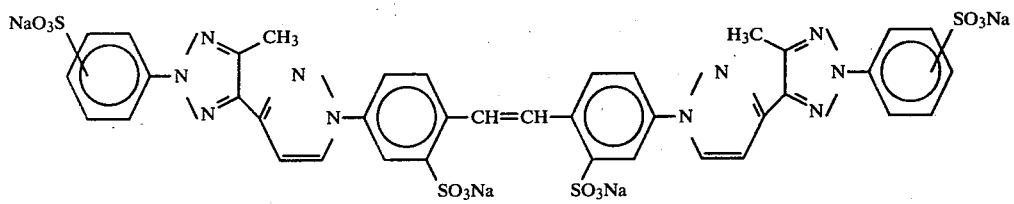

as a yellow powder.

EXAMPLE 42

The preparation of a pyrazole of the formula

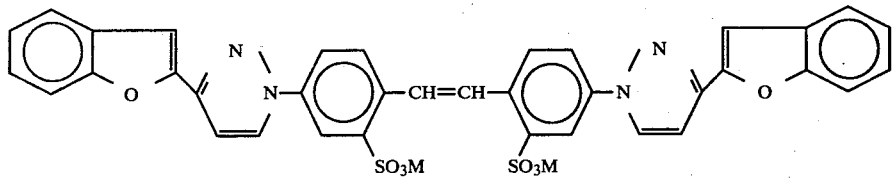

a yellow coloured powder.

(a) 2-(β-morpholinopropionyl)-benzofuran hydrochloride was prepared by the following procedure:

2-Acetyl benzofuran (40 g) [J.A.C.S. 73, 754 (1951)], paraformaldehyde (7.6 g) morpholine hydrochloride (30.8 g) and 2-ethoxyethanol (90 ml) were mixed and heated at reflux for 90 minutes. The reaction mixture was cooled to −10° C., filtered and the white coloured solid washed with ethyl alcohol (100 ml) to give 2-(β-morpholinopropionyl)benzofuran hydrochloride m.p. 210°–220° C.,

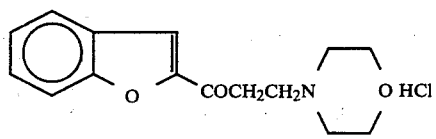

The pyrazole of the formula

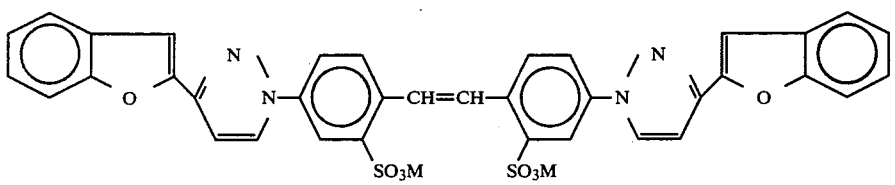

(where M = Na+)

a yellow coloured powder was prepared from the 2-(β-morpholinopropionyl)-benzofuran hydrochloride according to the method of part (c) of Example 1 where the 2-(β-morpholinopropionyl)-benzofuran hydrochloride is substituted for the hydrochloride of Example 1.

EXAMPLES 43–48

By using similar procedures to those described in Example 42 the following heterocyclic pyrazoles of general formula

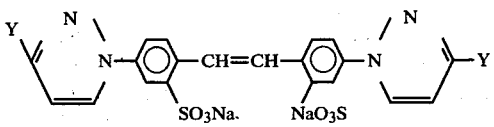

(where M = Na+)

are obtained.

| Example No. | Y | Appearance |
|---|---|---|
| 43 | Cl-benzofuran | bright lemon yellow powder |
| 44 | CH₃-benzofuran | yellow powder |
| 45 | CH₃O-benzofuran | bright lemon yellow powder |
| 46 | benzofuran | lemon yellow powder |
| 47 | benzothiophene | yellow-green powder |
| 48 | 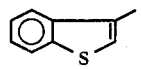 | yellow-green powder |

EXAMPLE 49

The production of a pyrazole triazole compound of the formula

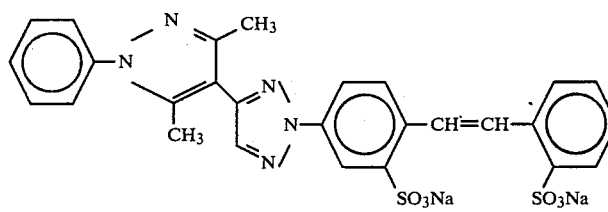

as a yellow coloured powder.

1-Phenyl-3,5-dimethyl-4-(2'-oximinoacetyl)-pyrazole was prepared as follows:

1-Phenyl-3,5-dimethyl-4-acetyl pyrazole (Chem. Abs. 63, 16332) (53 g) was dissolved in absolute ethanol (120 ml) and cooled to 7° C. Isopropyl nitrite (29.3 g) was added followed by a solution of sodium (5.7 g) in absolute ethanol (110 ml). The mixture was stirred 18 hours at 0°-10° C. and the fawn coloured sodium salt of the oxime filtered and washed with acetone (25 ml). The filter cake was then dissolved in water (40 ml) and the solution acidified with acetic acid (7 ml). The mixture was then extracted with chloroform (200 ml) and the chloroform extract dried over anhydrous sodium sulphate and then concentrated under vacuum to give 1-phenyl-3,5-dimethyl-4-(2'-oximino acetyl)-pyrazole as a yellow coloured solid.

A mixture of 4,4'-bis-hydrazino stilbene-2,2'-disulphonic acid (5.75 g), water (73 ml) and 40% W/V sodium hydroxide solution (5 ml) was treated at 40° C. with a solution of 1-phenyl-3,5-dimethyl-4-(2'-oximino acetyl)-pyrazole (7 g) in methanol (73 ml). The mixture was refluxed for 1 hour, concentrated to ca. half its volume and treated with pyridine (85 ml) and cupric sulphate pentahydrate (15.6 g). The mixture was refluxed for 4 hours, cooled to 80° C. and sodium sulphide dihydrate (6.9 g) added. The mixture was warmed to 90° C., filtered and the filtrates cooled. The precipitated triazole-N-oxide was filtered off and dried.

To a hot solution of the triazole-N-oxide (12.8 g) in water (30 ml), acetic acid (9 ml) and N,N-dimethylformamide (57.5 ml) was added zinc dust (9 g). The mixture was refluxed for 2 hours, filtered hot and the filtrates diluted with hot water, and cooled. The precipitated product was filtered off and crystallised from aqueous alcohol to give the pyrazole-triazole of formula

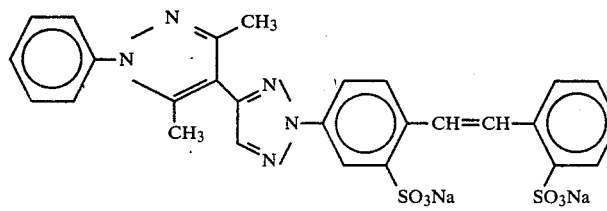

as a yellow coloured powder.

EXAMPLES 50 to 53

By using the equivalent amounts of 1-phenyl-3-methyl-4-acetyl pyrazole, 1-phenyl-4-acetyl pyrazole, 1-phenyl-5-methyl-4-acetyl pyrazole or 2-acetyl benzofuran in Example 49 the following heterocyclic triazoles of formula

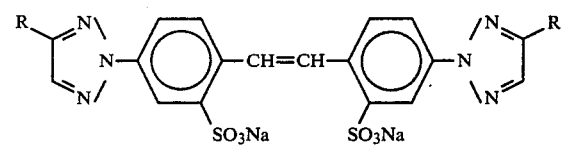

are obtained.

| Example No. | R | Appearance |
|---|---|---|
| 50 | CH₃-pyrazole-N-phenyl (3-methyl-1-phenyl) | Yellow-green powder |
| 51 | pyrazole-N-phenyl (1-phenyl) | Yellow-green powder |
| 52 | pyrazole-N-phenyl (5-methyl-1-phenyl) | Yellow-green powder |
| 53 | benzofuran-2-yl | Yellow powder |

EXAMPLE 54

4,4'-Diamino stilbene-2,2'-disulphonic acid (9.25 g) was dissolved in water (50 ml) and sodium carbonate (2.75 g). Concentrated hydrochloric acid S.G. 1.18 (12.5 ml) was added and the mixture cooled to 5°-10° C. Sodium nitrite (3.5 g) was then added during 1 hour at 5°-10° C. The tetrazonium salt suspension was then added during half an hour to a solution of 2 benzofuran propionic acid-β-oxoethyl ester (British Pat. No. 532,943) (12.06 g) in methanol (200 ml) and pyridine (50 ml) at 25°-30° C. The mixture was then stirred for 1 hour at 30°-35° C. and 30 minutes at 60° C. The orange coloured mixture was cooled to 5° C. and the hydrazone filtered and washed with water (200 ml) and dried.

The dried hydrazone (21.9 g) was mixed with 2-ethoxy ethanol (98.4 ml) propionic acid (29.2 ml), ammonia S.G.O. 880 (27 ml), cupric chloride dihydrate (14.7 g) and urea (29.8 g). The mixture was refluxed for 16 hours, 10% W/V sodium chloride solution (200 ml) added and the brown coloured mixture then cooled to 5° C., filtered and washed with water (200 ml). The brown coloured solid was mixed with water (100 ml) 2-ethoxy ethanol (100 ml) and 30% W/V sodium hydroxide solution (10 ml). The mixture was then refluxed for 30 minutes and mixed with sodium sulphide dihydrate (5 g) and sodium hydrosulphite (5 g). The precipitate cupric sulphide was screened and the filtrate evaporated to dryness under vacuum. The residue was then recrystallised from water to give the triazole of formula

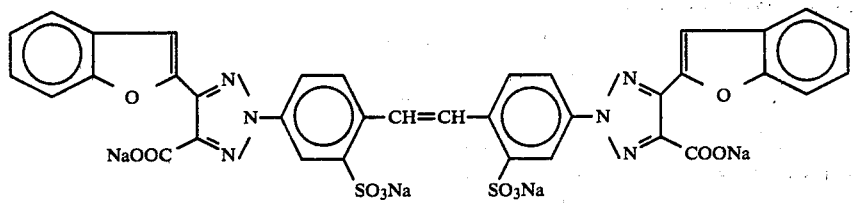

as a yellow coloured powder.

EXAMPLE 55

4.7 g of the triazole described in Example 54 was added to toluene (100 ml) and the mixture heated to 60° C. Dimethylformamide (0.5 ml) was added followed by thionyl chloride (4 ml). The mixture was heated 1 hour at 60°-70° C. and 30 minutes at reflux. Absolute ethanol (50 ml) was added and the mixture heated at reflux for 18 hours. The mixture was filtered at 70° C., washed with acetone (50 ml) and hot water (50 ml). The crude product was recrystallised from methoxy ethanol (105 ml) and water (45 ml) to give the triazole of formula

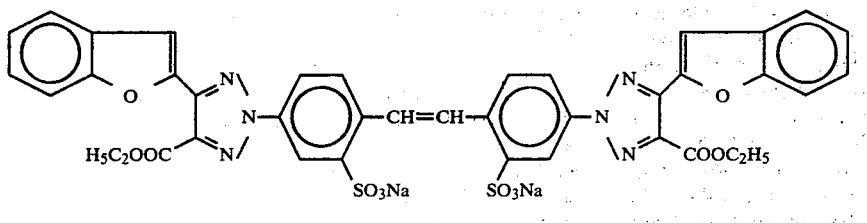

as a yellow coloured powder.

EXAMPLE 56

12 g of the compound described in Example 46 was was added to concentrated sulphuric acid S.G. 1.84 (60 mls) and the mixture heated for 1 hour at 90°-95° C. The solution was cooled to 20° C. and poured on to ice (300 g) and water (300 ml). Sodium chloride (30 g) was added and the yellow precipitate filtered and washed with 10% W/V sodium chloride solution (300 ml). The filter cake was dissolved in water (240 ml) and 30% W/W sodium hydroxide solution (20 ml) at 80° C. Sodium chloride (15 g) was added and the mixture cooled to 5° C. The yellow product was filtered and then dried at 80° C. to give the pyrazole of formula

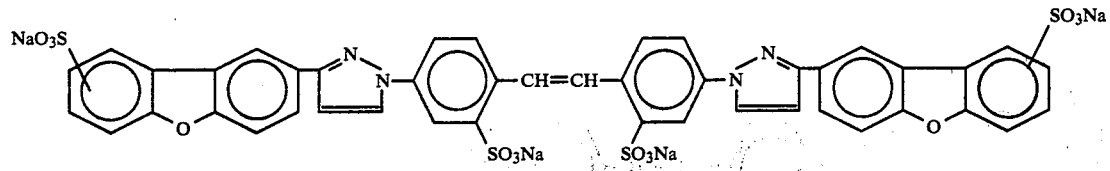

as a yellow coloured powder.

EXAMPLE 57

The preparation of a pyrazole of the formula

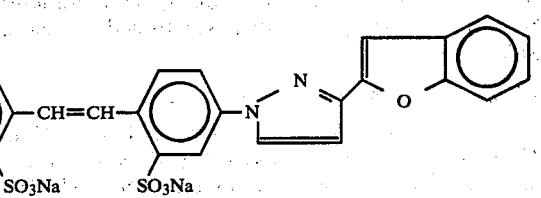

(a) 2-(α-sulpho acetyl)benzofuran sodium salt was prepared as follows:

2-(α-bromoacetyl)-benzofuran (100.7 g) (J.A.C.S.61 2705-8, 1939), water (300 ml) and anhydrous sodium sulphite (71.1 g) were mixed and refluxed for 30 minutes. The mixture was cooled, filtered and washed with 4% W/V sodium chloride solution (200 ml), then acetone (300 ml) and finally dried at 80° C. to give 2-(α-sulpho acetyl) benzofuran sodium salt

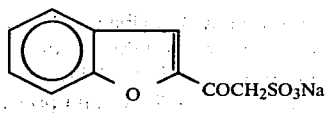

as a white coloured powder.

(b) 2-(α-sulpho-β-morpholinopropionyl)-benzofuran inner salt was prepared by the following procedure:

2-(α-sulpho acetyl)benzofuran sodium salt (70 g) morpholine (40.7 g), concentrated sulphuric acid S.G.1.84 (22 g) and ethyl alcohol (150 ml) were mixed and refluxed for 16 hours. The mixture cooled, filtered, washed with cold water (200 ml) and dried at 80° C. to give 2-(α-sulpho-β-morpholinopropionyl)-benzofuran inner salt

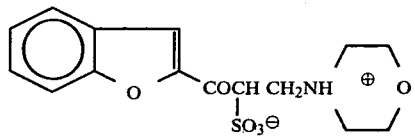

as a white coloured powder.

The pyrazole of the formula

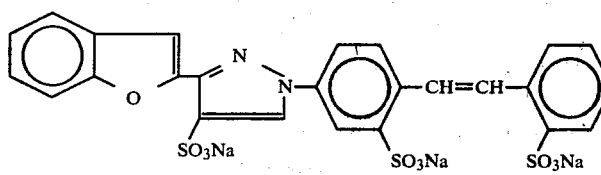

was prepared from the 2-(α-sulpho acetyl)benzofuran sodium salt according to the method of part (c) of Example 1, where the 2-(α-sulpho-β-morpholinopropionyl)benzofuran inner salt is substituted for the hydrochloride of Example 1.

Application Example A

A 5 gram piece of cotton was entered at 40° C. into 250 ml of a solution containing 1 g of sodium dodecyl benzene sulphonate based washing powder and 0.005 g of the compound described in Example 1. The temperature of the liquor was raised to 70° C. over 15 minutes and maintained at 70° C. for a further 30 minutes. The treated cloth samples were rinsed thoroughly in cold demineralised water and dried at 80° C. The cotton piece showed a brilliant neutral hued brightening compared with the untreated material.

Similar brightening effects were observed when the cotton was brightened at 30° C., 50° C. and 90° C.

Application Example B

A 5 gram piece of cotton was entered at ambient temperature into 200 ml of an aqueous solution containing 25 mg of the compound described in Example 1 and 500 mg hydrated sodium sulphate. The cotton was agitated whilst the temperature was raised to 70° C. over 15 minutes, and maintained at 70° C. for a further 30 minutes after which it was removed from the bath, rinsed thoroughly in cold water, spun dry and dried in an oven at 80° C. The treated fabric showed a billiant whiteness compared with the untreated cotton.

Application Example C

A 5 gram piece of cotton was entered at 40° C. into 250 ml of a solution containing 1 gram of sodium dodecyl benzene sulphonate based washing powder, 25 mg of active chlorine (added as sodium hypochlorite solution) and 0.005 g of the compound described in Example 15. The temperature of the wash liquor is raised to 50° C. over 15 minutes and maintained at 50° C. for a further 30 minutes. The treated cloth samples were rinsed thoroughly in cold demineralised water and dried at 80° C. The cotton piece showed a brilliant neutral hued brightening compared with the untreated material.

Application Example D

A 5 gram piece of cotton was entered at 40° C. into 250 ml of a solution containing 1 g of sodium dodecyl benzene sulphonate based washing powder and 0.005 g of the compound described in Examples 32 or 46. The temperature of the liquor was raised to 70° C. over 15 minutes and maintained at 70° C. for a further 30 minutes. The treated cloth samples were then rinsed thoroughly in cold demineralised water and dried at 80° C. The cotton piece showed a brilliant greenish hued brightening compared with the untreated material.

Application Example E

A strip of cotton, 20 cm wide and weighing 10 grams, was padded at 80% expression through a solution containing 0.3% of the compound prepared in Example 41, 7% of Glaubers salt, 7.5% of a carbamide resin pre-condensate, 0.03% of an ethylene oxide condensate of an alkylated phenol, and 1.5% zinc nitrate hexahydrate. The cotton piece was dried at 80° C., then kept in an oven at 160° C. for 5 minutes. The treated fabric was crease-resistant and showed brilliant whiteness compared to the untreated cotton.

Application Example F

A 5 gram piece of nylon 6,6 (Banlon) was treated with 200 ml of a solution containing 25 mg of the compound described in Example 42, 400 mg of sodium chlorite, and 1.5 ml of 10% W/V acetic acid. The solution was buffered to pH 3.5. The buffer mixture contained 4 ml of a 10% W/V phosphate based buffer salt and 2.5 ml 10% formic acid. The nylon piece was entered into the liquor at 40° C. The temperature of the liquor was raised to 90°-95° C. over 30 minutes and maintained at 90°-95° C. for a further 30 minutes. The fabric was then rinsed in cold demineralised water, then in a 0.1% aqueous solution of sodium metabisulphite and again thoroughly rinsed in cold demineralised water, and finally dried at 80° C. The treated piece showed a brilliant neutral hued brightening compared with the untreated material.

Application Example G

A 5 gram piece of nylon 6,6 (Banlon) was entered at room temperature into a solution containing 10 ml of 10% W/V acetic acid, 190 ml water and 25 mg of the compound described in Example 42. The temperature was raised to 90° C. over 30 minutes and maintained at 90°–95° C. for a further 30 minutes, during which time the fabric was agitated mechanically. The fabric was then removed from the liquor, rinsed thoroughly in cold water, spun dry and dried in an oven at 80° C. The treated fabric showed a brilliant whiteness compared with the untreated material.

What is claimed is:

1. A compound of the formula

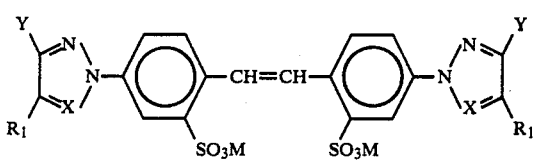

I in which
both $R_1$'s are the same and are hydrogen, $C_{1-4}$alkyl, bromine, chlorine, —COOM, —CONR$_2$R$_3$, —COOR$_4$, —CN, —SO$_3$M, —SO$_2$NR$_2$R$_3$ or —SO$_2$R$_4$, where $R_2$ and $R_3$ independently are hydrogen, $C_{1-4}$alkyl or phenyl with the proviso that only one may be phenyl or $R_2$ and $R_3$, together with the nitrogen to which they are attached, form piperidine or morpholine ring and $R_4$ is $C_{1-4}$alkyl or phenyl;
both X's are the same and are CR$_5$ or N, where R$_5$ is hydrogen, $C_{1-4}$alkyl or phenyl;
both Y's are the same and are each one of the radicals of formulae (a) to (e)

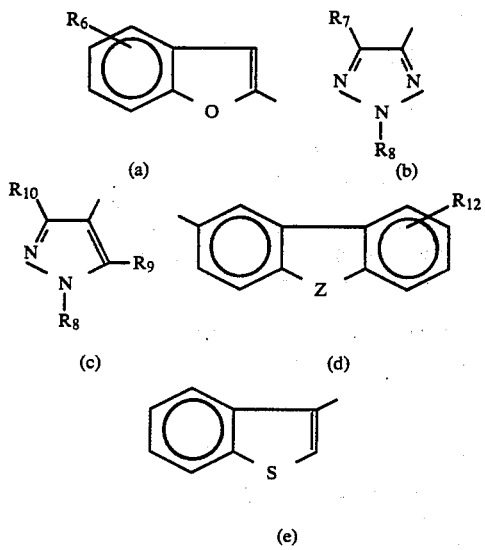

with the proviso that the Y's are not radical (b) when X=N, $R_6$ is hydrogen, chlorine, $C_{1-4}$alkoxy, $C_{1-4}$alkyl, —SO$_3$M or phenyl, $R_7$ is hydrogen or $C_{1-4}$alkyl, $R_8$ is an aryl radical unsubstituted or substituted by up to two substituents selected from $C_{1-4}$alkyl, $C_{1-4}$alkoxy, chlorine, cyano, —COOM, —COOR$_4$, —CONR$_2$R$_3$, —SO$_2$NR$_2$R$_3$, —SO$_2$R$_4$ and —SO$_3$M with the proviso that where the aryl radical is substituted by two substituents at least one of the substituents is $C_{1-4}$alkyl, $C_{1-4}$alkoxy or chlorine, $R_9$ and $R_{10}$ independently are hydrogen or $C_{1-4}$alkyl; $R_{12}$ is H or —SO$_3$M and Z is O or S; and M is hydrogen or a non-chromophoric cation.

2. A compound according to claim 1 in which Y is any one of the radicals a' to d'

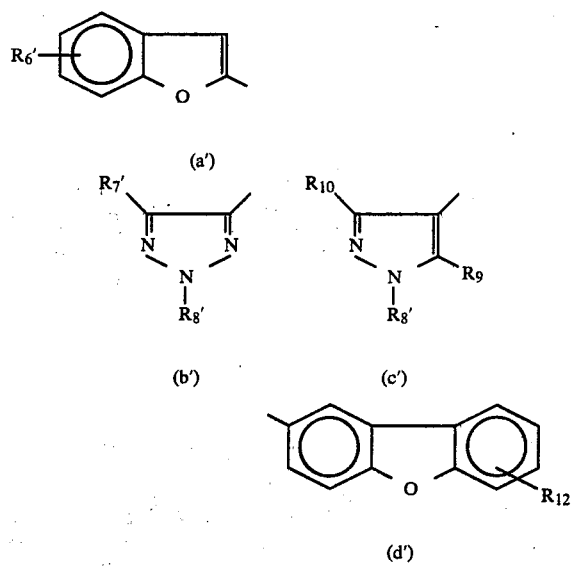

where $R_9$, $R_{10}$ and $R_{12}$ are defined in claim 1 and in which
$R_6'$ is hydrogen, chlorine, $C_{1-4}$alkyl or $C_{1-4}$alkoxy;
$R_7'$ is hydrogen or methyl; and
$R_8'$ is phenyl or naphthyl unsubstituted or substituted by 1 or 2 substituents selected from $C_{1-4}$alkyl, $C_{1-4}$alkoxy, chlorine or —SO$_3$M with the proviso that when disubstituted both substituents cannot be —SO$_3$M.

3. A compound according to claim 2 of formula I'

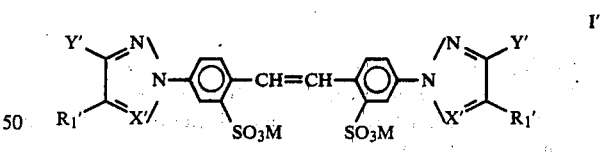

in which
Y' is defined in claim 2;
$R_1'$ is hydrogen, methyl, chlorine, —COOM, —SO$_3$M or COOR$_4$;
X' is CR$_5'$ or N where R$_5'$ is hydrogen or methyl; and
M is hydrogen or a non-chromophoric cation.

4. A compound according to claim 2 of formula I"

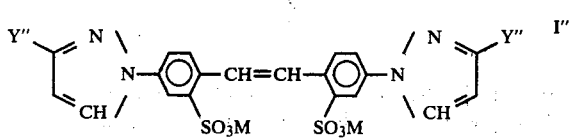

in which Y" is d' as defined in claim 2 or one of the radicals a" to c"

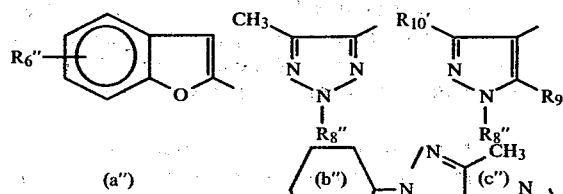
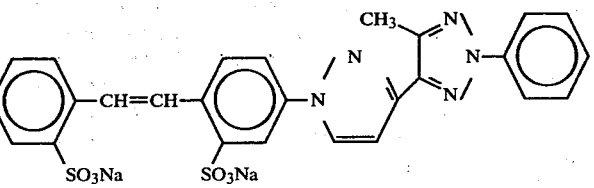

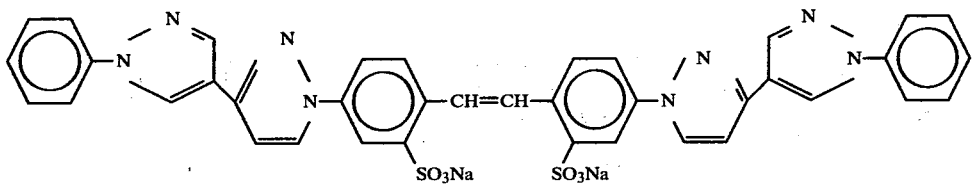

of the formula

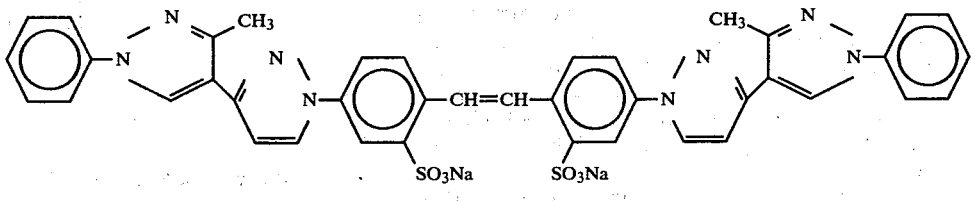

of the formula

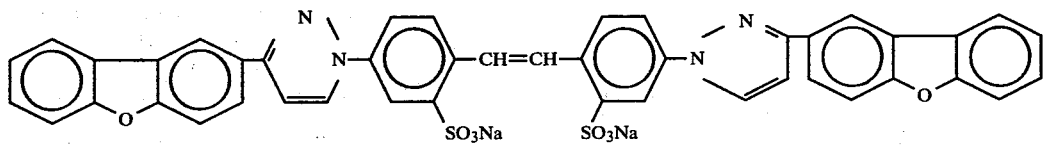

of the formula

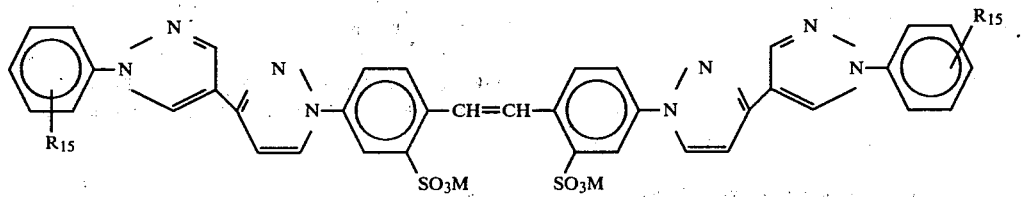

where
R$_6''$ is hydrogen, chlorine, methyl or methoxy;
R$_8''$ is phenyl unsubstituted or substituted by 1 or 2 substituents selected from methyl, methoxy, chlorine or —SO$_3$M,
R$_9'$ and R$_{10}'$ are hydrogen or methyl.

5. A compound according to claim 2 of the formula in which M is hydrogen or a non-chromophoric cation and the groups R$_{15}$ are independently hydrogen, C$_{1-4}$alkyl, C$_{1-4}$alkoxy, chlorine, cyano, —COOM, —COOR$_4$, —CONR$_2$R$_3$, —SO$_2$NR$_2$R$_3$, —SO$_2$R$_4$, —SO$_3$M in which R$_2$ and R$_3$ are independently hydrogen, C$_{1-4}$alkyl or phenyl with the proviso that only one may be phenyl or R$_2$ and R$_3$ together with the nitrogen atom to which they are attached form a five or six membered heterocyclic ring and R$_4$ is C$_{1-4}$alkyl or phenyl.

6. A compound according to claim 1 of the formula

7. A substrate when brightened with a compound of formula I defined in claim 1.

8. A compound according to claim 1 wherein X is N, R$_1$ is R$_1''$ where R$_1''$ is hydrogen, —COOM or COOR$_4'$ and R$_4'$ is C$_{1-4}$alkyl, or X is CR$_5$ and R$_1$ is R$_1'''$ where R$_1'''$ is hydrogen or —SO$_3$M.

9. A compound according to any of claims 1, 2, 3, 4, 5 or 8 wherein any non-chromophoric cation as M is an alkali metal, an alkaline earth metal, ammonium, alkylammonium or alkanolammonium.

10. A substrate according to claim 7 which is polyamide or cellulosic.

* * * * *